United States Patent
Feiweier et al.

(10) Patent No.: US 9,055,882 B2
(45) Date of Patent: Jun. 16, 2015

(54) METHOD AND APPARATUS TO GENERATE MAGNETIC RESONANCE IMAGES

(75) Inventors: Thorsten Feiweier, Poxdorf (DE); Martin Harder, Nuremberg (DE); John Kirsch, Charlestown, MA (US); Wilfried Landschuetz, Baiersdorf (DE); Andreas Schmidt, Erlangen (DE); Katrin Wohlfarth, Erlangen (DE)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 568 days.

(21) Appl. No.: 13/456,739

(22) Filed: Apr. 26, 2012

(65) Prior Publication Data

US 2013/0285654 A1 Oct. 31, 2013

(51) Int. Cl.
*A61B 5/055* (2006.01)
*G01R 33/54* (2006.01)
*G01R 33/483* (2006.01)
*G01R 33/565* (2006.01)

(52) U.S. Cl.
CPC .............. *A61B 5/055* (2013.01); *G01R 33/4833* (2013.01); *G01R 33/543* (2013.01); *G01R 33/56563* (2013.01)

(58) Field of Classification Search
CPC ............. G01R 33/485; G01R 33/4828; G01R 33/4808; G01R 33/543; G01R 33/4833; G01R 33/56563

See application file for complete search history.

(56) References Cited

U.S. PATENT DOCUMENTS

| | | | | |
|---|---|---|---|---|
| 4,847,559 A * | 7/1989 | Keren | | 324/307 |
| 5,560,360 A * | 10/1996 | Filler et al. | | 600/408 |
| 5,657,758 A * | 8/1997 | Posse et al. | | 600/413 |
| 5,709,208 A * | 1/1998 | Posse et al. | | 600/410 |
| 7,869,562 B2 * | 1/2011 | Khamene et al. | | 378/20 |
| 8,384,771 B1 * | 2/2013 | Douglas | | 348/53 |
| 8,598,876 B2 * | 12/2013 | Rapoport | | 324/309 |
| 2010/0286802 A1 | 11/2010 | Feiweier et al. | | |

OTHER PUBLICATIONS

"Concomitant Field Terms for Asymmetric Gradient Coils: Consequences for Diffusion, Flow, and Echo-Planar Imaging," Meier et al., Magnetic Resonance in Medicine, vol. 60 (2008) pp. 128-134.

* cited by examiner

*Primary Examiner* — Dixomara Vargas
(74) *Attorney, Agent, or Firm* — Schiff Hardin LLP

(57) ABSTRACT

In a method and apparatus to generate a magnetic resonance (MR) image in a volume of interest of an examination subject, the magnetization is excited in an additional volume in the subject by at least one RF pulse, in order to achieve a desired magnetization in the volume of interest. The additional excitation volume differs at least partially from the volume of interest. For this purpose, at least one MR overview image of the examination subject is analyzed automatically to determine a position of at least one anatomical structure of the examination subject, from which the volume of interest is automatically determined. The additional excitation volume is automatically determined using the position of the at least one anatomical structure. The MR image in the volume of interest is acquired with excitation of the magnetization in the automatically determined additional excitation volume.

15 Claims, 4 Drawing Sheets

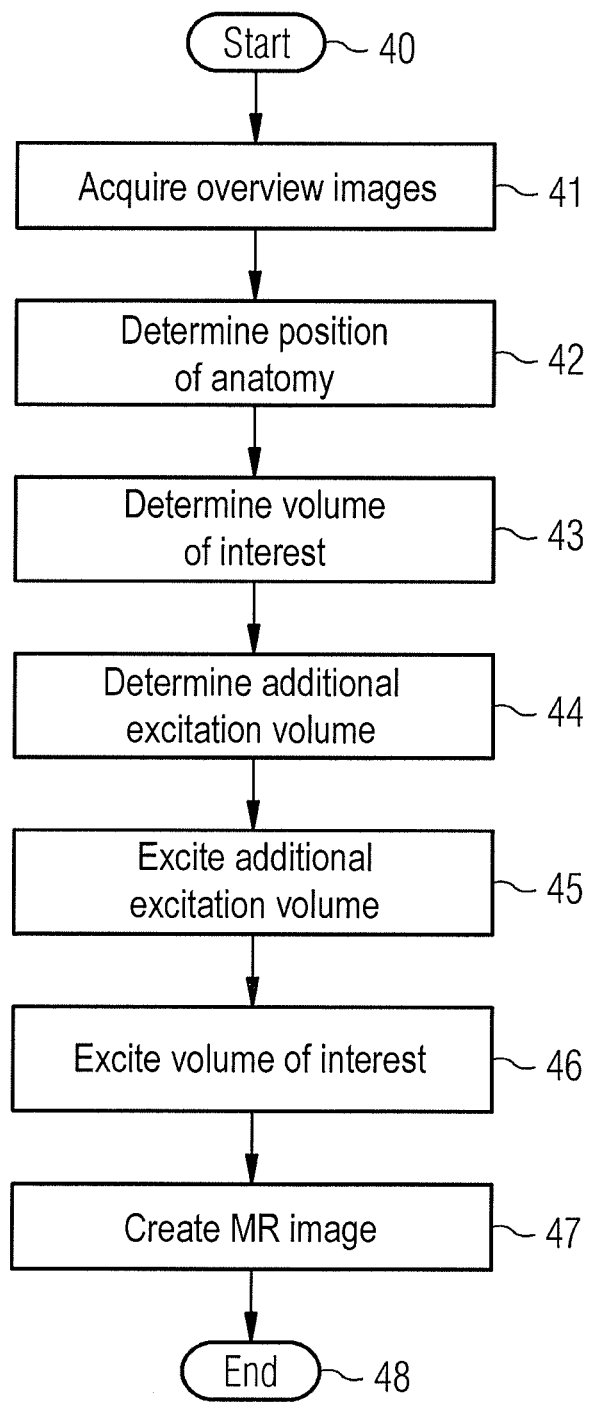

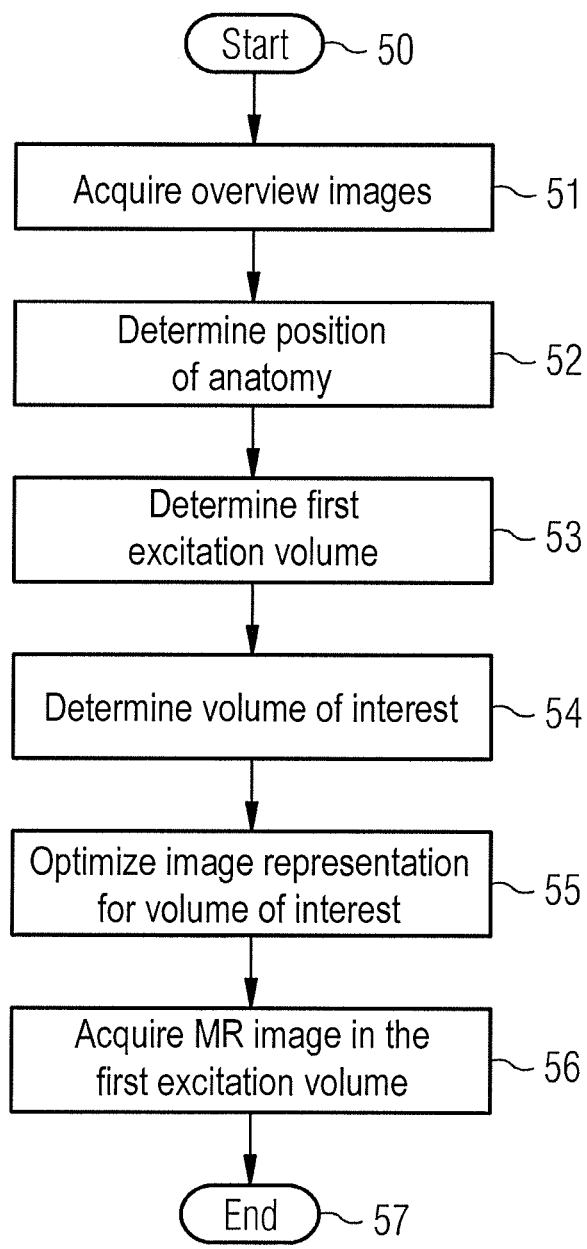

METHOD AND APPARATUS TO GENERATE MAGNETIC RESONANCE IMAGES

BACKGROUND OF THE INVENTION

1. Field of the Invention

The present invention concerns a method to generate magnetic resonance (MR) images in a volume of interest of an examination subject, and a method to generate an MR image of a first excitation volume of the examination subject, as well as an MR system to implement such methods.

2. Description of the Prior Art

The optimization of the image quality represents one of the central themes in the development of tomographic imaging modalities such as magnetic resonance (MR) systems. In a typical examination workflow, an overview image (known as a localizer image or simply "localizer") is initially acquired in which the actual diagnostic measurements for the generation of MR images are then planned, with which MR images a physician wishes to answer a desired medical question. In addition to the selection of suitable contrast parameters such as the sequence type or sequence parameters (such as echo time TE, repetition time TR), the extent, attenuation and position of the acquisition volume is thereby established, meaning that a first excitation volume in which the magnetization is excited and that is then shown in the MR image is established. For example, this first excitation volume can encompass a number of slices in the case of a two-dimensional imaging, or can be in the form of blocks in a three-dimensional imaging.

Additional excitation volumes in which the magnetization of nuclear spins is excited (also called active volumes in the following) can result, for example, by the establishment of local saturation regions, for example for the suppression of unwanted image regions. This suppression can be desirable if movement, flow or pulsations are to be expected, for example. Additional excitation volumes are local or global preparation volumes—for example the suppression of the fat signal in the total examination volume—or local marking volumes, for example to mark incoming blood for contrast agent-free determination of flow or perfusion. The acquisition volume—i.e. the first excitation volume—often encompasses a markedly larger region than the actual volume of interest. The volume of interest is the volume in which an assessing physician wishes to obtain information to clarify a medical question. For example, the volume of interest can include a potential pathology. The reasons that the first excitation volume is larger than the volume of interest lie first in that (among other things) the possibility for fast orientation in the anatomy is desired, and second in that the aliasing artifacts should be avoided. However, such a large acquisition volume can be accompanied by a reduced image quality in the volume of interest. The control of all technical acquisition modules is optimized for the acquisition of the first excitation volume, which automatically entails a compromise for the volume of interest.

An additional disadvantage of the aforementioned planning method is the long time cost for the planning of the individual excitation volumes.

The limitation of the acquisition volume to the volume of interest is possible in principle, for example via a selective spatial excitation of this volume. However, the possibility for fast orientation in the anatomy is hereby lost. Furthermore, such selective excitations are frequently linked with additional disadvantages, for example a longer echo time and a longer acquisition time connected with this. The volume of interest is typically established manually by the user. In addition to the first excitation volume, the acquisition volume of possible additional excitation volumes are thereby established by the user in the overview image with a graphical user interface with regard to attitude, orientation and position. However, an experienced user is necessary for this; the placement of the individual volumes is poorly reproducible and costly in terms of time. Furthermore, the automatic establishment of individual excitation volumes (called working volumes there) is known from DE 10 2009 020 661 A1.

SUMMARY OF THE INVENTION

An object of the present invention is to reproducibly improve the image quality in the volume of interest, wherein (among other things) the time cost for planning the measurement should be reduced.

According to a first aspect of the invention, a method is provided to generate an MR image that includes a volume of interest of an examination subject, wherein a medical question should be answered in the volume of interest with the MR image to be created. The examination subject has an additional excitation volume in which the magnetization is excited via at least one MR pulse in order to achieve a desired magnetization in the volume of interest. The additional excitation volume differs at least partially from the volume of interest. In one step of the method, at least one acquired MR overview image of the examination subject is analyzed to automatically determine an attitude of at least one anatomical structure that is comprised the examination subject. Furthermore, the volume of interest and the additional excitation volumes are determined automatically using the determined attitude of the at least one anatomical structure. In a further step, the MR images or the MR image is or are subsequently acquired in the volume of interest, wherein the excitation takes place in the automatically determined additional excitation volume. The excitation of the magnetization in the excitation volume typically takes place chronologically before the excitation of the magnetization in the volume of interest in order to have a desired effect in the acquisition of the multiple signals in the volume of interest with the excitation in the additional excitation volume; however, it can also take place simultaneously or afterward. The volume of interest can be determined either automatically or manually by the user.

The invention thus enables the automatic adaptation of the additional excitation volume (and possibly of the volume of interest) depending on the attitude of the automatically detected anatomical structure. In particular, the attitude of the additional excitation volume can be reproduced via the automatic determination of the additional excitation volume, which is not necessarily depicted in the MR image to be created. For example, the excitation volume can include a local saturation volume to suppress a signal of unwanted image regions. Furthermore, the excitation volume can be a preparation volume, for example for the preparation of blood that flows into the volume of interest.

In the generation of the MR image that depicts the volume of interest, an MR image of a first excitation volume can be generated that is greater than the volume of interest and which includes the volume of interest.

It is possible for an RF transmission module, which has components to emit the RF pulses to produce the magnetization, to be optimized for the volume of interest. In addition to the transmission module, the reception module can also be optimized for the volume of interest and not for the first excitation volume. Furthermore, the magnetic field homogeneity for generation of the magnetization with the use of a polarization field B0 in the examination subject can be optimized for the volume of interest, and not for the larger first excitation volume. In these aforementioned aspects, the adaptation of the transmission and reception system of the MR system to the volume of interest (which is smaller than the first excitation volume shown in the image) takes place. By the matching of the individual MR components to the smaller volume of interest, and not to the first excitation volume (representing the entire image), the image quality can be improved in the volume of interest; for example, the contrast can be improved since less consideration must be made for the volume proportions that, although they are included in the MR image, are not in the volume of interest where the physician wishes to have a best possible image quality to clarify a medical question.

The magnetization in the additional excitation volume can be excited such that the influence of the magnetization from the additional excitation volume on the volume of interest is optimized in the acquisition of the MR image of the volume of interest. For example, this can mean to minimize the influence of the magnetization from the additional excitation volume, for example to saturate unwanted signal components; or, it can be desired to excite the magnetization in the additional excitation volume such that the magnetization flowing into the volume of interest differs from the prevailing stationary magnetization in the volume of interest. For example, this can be advantageous given angiography measurements or measurements to determine the flow velocity.

The invention likewise concerns a magnetic resonance system to generate MR images in a volume of interest that operates according to the method described above.

The invention furthermore concerns a method to generate an MR image of a first excitation volume of an examination subject, wherein the first excitation volume has the volume of interest, and the volume of interest is a partial volume of the first excitation volume, and therefore is smaller than the first excitation volume. According to one step of the method, at least one MR overview image of the examination subject that is acquired is analyzed in order to determine an attitude of at least one anatomical structure that is included in the examination subject. Furthermore, the first excitation volume and the volume of interest are automatically determined using the attitude of the at least one anatomical structure. In a further step, the automatic optimization of a signal acquisition to create the MR image that depicts the first excitation volume specifically takes place for the volume of interest, and not for the first excitation volume.

By the automatic determination of the first excitation volume and the volume of interest using the detected anatomy and the optimization of the MR signal acquisition for the volume of interest, on the one hand reproducible volumes are achieved, and on the other hand it is possible to increase the image quality (and therefore the significance) in the volume of interest. Since the optimization (for example of the signal transmission chain and the reception chain) is implemented for the volume of interest and not for the larger first excitation volume that is shown in the MR image, overall the image quality is improved since no compromises need to be made any more for regions outside of the volume of interest that, although they are included in the MR image, can accept a suboptimal contrast from a diagnostic point of view. In addition to the optimization of the RF transmission module and the RF reception module for the volume of interest and the magnetic field homogeneity of the polarization field B0, the magnetic field gradient can also be optimized for the volume of interest, for example. For example, the compensation of the linear portions of accompanying Maxwell fields can also be optimized for the volume of interest. For example, care can be taken that the influence of the linear portion is reduced by switching corresponding compensation magnetic field gradients, in particular in the volume of interest (not in the entire excitation volume). In the same way, the constant portion can be reduced by switching a corresponding compensation frequency offset in the transmission and reception module.

The physics underlying such optimization is described by C. Meier, M. Zwanger, T. Feiweier and D. Porter: "Concomitant field terms for asymmetric gradient coils: consequences for diffusion, flow and echo-planar imaging", Magnetic Resonance in Medicine, 2008, Vol. 60, pp. 128-134, for example.

Furthermore, it is possible that the first excitation volume has a volume of interest that is divided up into multiple partial volumes. For example, in an MR mammogram the MR system can be optimized for the attitude of the left breast and right breast, wherein the optimization takes place specifically for the two partial volumes and not in the entire shown region (which possibly includes the entire ribcage)

The invention furthermore encompasses a magnetic resonance system to generate an MR image of the first excitation volume that operates as described above.

BRIEF DESCRIPTION OF THE DRAWINGS

FIG. 4 is a flow chart with the steps to automatically determine the volume of interest and the additional excitation volume.

FIG. 5 is a flow chart with the steps to optimize the acquisition for a partial region of the shown volume.

DESCRIPTION OF THE PREFERRED EMBODIMENTS

Figure 1:
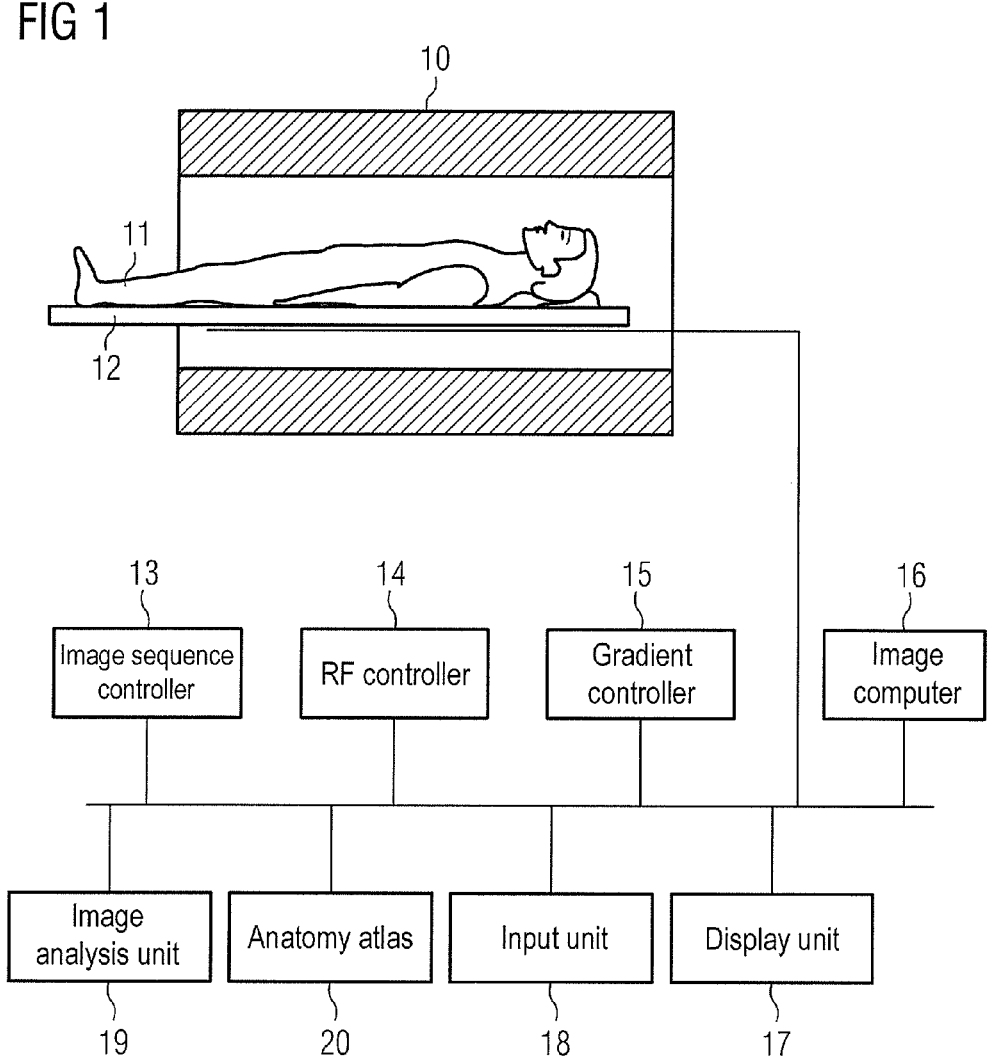
FIG. 1 schematically illustrates an MR system according to the present invention.

In FIG. 1 an MR system is shown with which an image quality in a volume of interest is improved and with which an automatic determination of the volume of interest and an additional excitation volume is possible using the anatomy.

The MR system has a magnet 10 to generate a polarization field B0. A person 11 to be examined who is arranged on a bed 12 is driven into the magnet, wherein a resulting magnetization of the nuclear spins in the body of the examined person 11 is generated, said magnetization pointing in the direction of the B0 field. The MR system has a gradient coil (not shown) to generate magnetic field gradients; at least one RF transmission coil; and at least one acquisition coil with which the MR signals induced by switching RF pulses and gradient pulses are detected. These transmission and reception units are likewise not shown for reasons of clarity. How MR images can be generated with a sequence of RF pulses in connection with magnetic field gradients is known to those skilled in the art and need not be explained in detail herein.

The MR system furthermore has an image sequence controller 13 with which the timing and configuration of the RF pulses and gradients is established, depending on the selected imaging sequence. The generation of the RF pulses themselves takes place via an RF controller 14; the generation and switching of the gradient fields takes place via a gradient controller 15. As mentioned above, the image sequence controller is responsible for the time sequence of the individual components and therefore also controls the RF controller 14 and the gradient controller 15. As is known to those skilled in the art, the signals detected by the reception coils are processed further and can be used in an image computer 16 to calculate (reconstruct) an MR image that can be presented at a display unit 17. An operator can control the functionality of the MR system via an input unit 18; for example, imaging sequences can be selected, imaging parameters such as echo time or the like can be set. The image planes can likewise be adjusted manually if necessary.

The MR system furthermore has an image analysis unit 19 with which overview images of the examined person 11 that are acquired by the MR system can be analyzed in order to identify an anatomical structure in the overview image or the overview images. For example, the image analysis unit 19 can use image processing algorithms in order to detect specific anatomical structures in the overview images. The anatomical structures to be determined can be predetermined by the operator of the MR system. By comparing the detected anatomical structures with atlases in an anatomy atlas 20, which region is shown in the overview image of the examined person can be established automatically. The different body regions with their various anatomical structures can be included in the anatomy atlas, and anatomical structures can be identified via comparison of the overview images with the anatomy atlas. For example, if an operator enters an input via the input unit 18 indicating that an MR exposure of the spinal column should be generated, the spinal column can be detected automatically in the overview image, and a volume of interest can be established automatically by the image sequence controller 13 or by an operator. If a medical question at the spinal column should be clarified, it is thus possible to limit the volume that is depicted in the later MR image (known as the first excitation volume) to the region of the spinal column. This is presented as an example in FIG. 2, in which the spinal column 22 was automatically identified in an overview image 21 of the examined person. The image sequence controller can then automatically establish the volume 23 of interest (represented here by the cuboid).

However, it is also possible that the first excitation volume that is shown in the MR image to be created is so large that it also includes the additional excitation volume. The first excitation volume would then be shown as large as in the overview image 21, for example. In the event that it is larger than the volume of interest, the first excitation volume can be established either manually by the operator or similarly by the image sequence controller.

However, in addition to the volume of interest 23, the image sequence controller can establish a further excitation volume 24 depending on the detected anatomy. The magnetization is excited in this further excitation volume; however, the volume of the further excitation volume is not included in the volume of interest or, respectively, first excitation volume as mentioned above. In the example shown in FIG. 2, it is desirable to suppress the signal portions from the abdominal wall in the generation of the MR image of the volume 23 of interest since here artifacts can arise in the volume of interest of the spinal column, for example due to the breathing motion. The further excitation volume can be included in the first excitation volume (that is shown in the MR image) or not. With the automatic selection of the volume of interest it is established where an optimal contrast is desired from a diagnostic standpoint, and where a non-optimal contrast can be tolerated (in the further excitation volume 24, for example).

Figure 2:
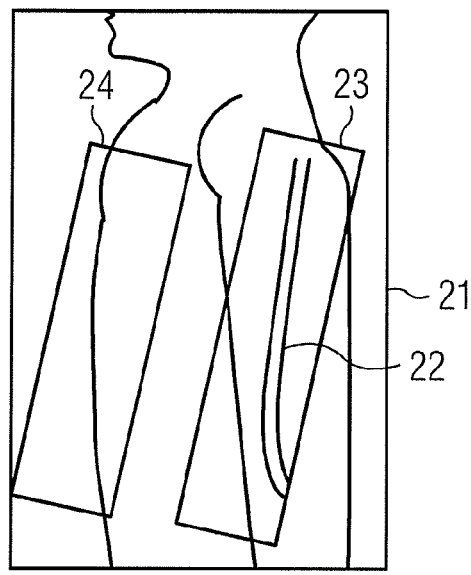
FIG. 2 shows an MR image with a volume of interest and an additional excitation volume, wherein the two volumes are determined automatically.

Naturally, the automatically determined volume of interest and additional excitation volumes are not limited to cuboid geometries as shown in FIG. 2. Other geometries are also possible. In the example shown in FIG. 2, the further excitation volume is thus determined due to the attitude, extent and orientation of the abdominal wall (what was detected automatically in the overview image). In the further excitation volume, the signal is saturated in order to suppress the signal from this region and in order to reduce movement artifacts.

In summary, for the example of FIG. 2 this means that the further excitation volume is either included in the first excitation volume (which is shown in the MR image) or not.

One example in which the further excitation volume is not included in the volume of interest is the application of the invention in the head to determine the perfusion of the individual regions in said head. For this, the position of the arteries (such as the aortas to the head) is identified and the magnetization in the aortas to the head is inverted in order to subsequently be able to identify the influence of the spins flowing into the head in the individual regions of the brain. According to the invention, it is now possible for the anatomy to be detected automatically in the overview images, such that the further excitation region (here the inversion region) in the aortas to the head is established automatically using the detected anatomy, along with the volume of interest in the head.

To further improve the image quality (for example the contrast), it is possible to optimize the MR system for the volume of interest and not for the shown first excitation volume. In addition to the contrast as a parameter for the image quality, in the volume of interest the signal-to-noise ratio can be optimized, or the suppression of unwanted signal contributions (for example the fat suppression) is optimized for this region. In the event that the volume of interest is smaller than the first excitation volume shown in the image, for example, it is possible to optimize the field homogeneity of the B0 field or of the B1 field only for the volume of interest and not for the excitation volume shown as a whole. Via what are known as shim coils it is possible to further improve the basic field homogeneity when the examined person is situated in the MR system. For example, if a chemically selective fat suppression should take place in the volume of interest, a good basic field homogeneity in the region of interest is necessary that, however, does not need to exist outside of the volume of interest. For example, the subcutaneous fat located there does not need to be suppressed perfectly. With regard to the example of FIG. 2, this can mean that the fat suppression in the region of the spinal column is optimized; however, the fat suppression in the abdominal wall is not very important.

Figure 3:
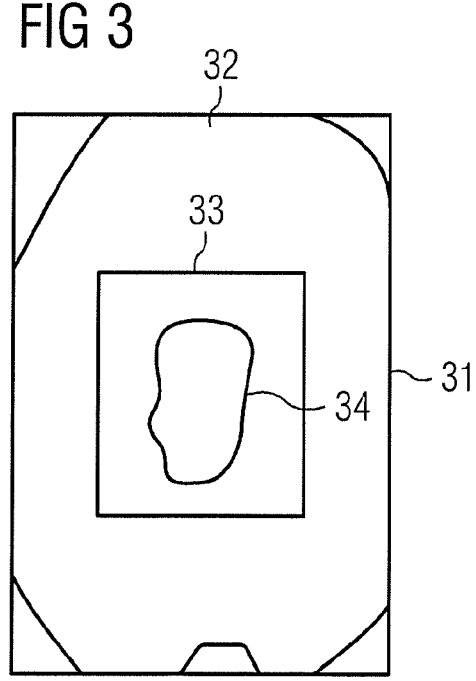
FIG. 3 shows an MR image with a first excitation volume and the volume of interest contained therein, wherein the optimization of the MR system for the volume of interest takes place.

Such an MR image is shown in FIG. 3. The MR image 31 shows a defined section of the anatomy in the examined person, wherein the first excitation volume 32 shown in the MR image 31 is larger than the volume 33 of interest. The MR image 31 is no longer the overview image, but rather represents the MR image with which the observing physician wishes to draw information from the volume 33 of interest.

According to this aspect of the invention, the first excitation volume 32 is first determined automatically using the attitude of the identified anatomical structure, and the volume of interest (here the volume 33) that includes the organ 34 and the immediate environment is determined automatically. To optimize the image quality in the volume of interest, the MR system is now optimized for the volume of interest and not (as has been typical) for the first excitation volume 32 shown in the MR image. For this purpose, in addition to the homogeneity of the basic magnetic field that was already mentioned above, an optimization of the geometric imaging fidelity can take place for this with compensation of Maxwell fields, relative to the partial volume 33. An additional way to optimize the image quality in the volume of interest is the optimization of the transmission branch and the reception branch of the MR system, meaning the adjustment of the transmission frequency, the adaptation of the transmission unit, the RF amplitudes and the magnetic field gradients, limited to the volume of interest and not to the first excitation volume shown in the MR image. The volume 33 of interest can be formed by or include two partial volumes. For example, the position of the left and right breasts can be identified, such that these volumes of interest are optimized simultaneously or sequentially during a measurement, meaning that the homogeneity of the B0 field and the B1 fields of the RF field are limited to achieve a homogeneous contrast, optimized for the two partial volumes. According to this aspect of the invention, an improvement of the image quality takes place via a targeted optimization of the technical transmission and reception modules of the MR system for anatomically relevant volumes of interest, and not for the entire volume shown in the MR image.

A flow chart that summarizes the steps to determine the volume of interest and the further excitation volume is shown in FIG. 4. The method starts in Step 40, and in Step 41 the overview image or overview images is or are acquired. In Step 42, the position of the relevant anatomical structure or of the multiple structures is determined. For example, the operator can establish which anatomical region is of interest, for example by selecting a measurement protocol that is titled accordingly, or even in the registration of the patient. An additional possibility would be to click on a structure in a schematic representation of the body. As is explained in connection with FIG. 1, for example, the anatomical structure is determined via comparison with reference images, for example. One possibility is hereby the comparison with atlases. In this the anatomy to be identified is acquired with the identical reference measurement from a plurality of subjects with different stature and age, and from this an averaged anatomical image—an atlas—is determined. The reference measurement of the patient is then compared with this atlas with the use of static methods, and in this way the attitude and orientation of the sought anatomy is determined. An additional possibility is the use of landmarks. Reference measurements of a number of subjects are likewise acquired. In these images, distinctive anatomical structures are recognized automatically; an algorithm for the reliable detection of these landmarks is trained by means of a monitored learning process. The algorithm is subsequently in the position to reliably detect the sought anatomy in the reference measurement. It is likewise conceivable to operate with a modeling of the anatomy; for example, a model of the heart or liver anatomy as a region of interest is created on the basis of contours, and the axes of the organ are then determined in this model.

In Step 43 the volume of interest is determined, i.e. the volume in which a defined question should be clarified. Furthermore, in Step 44 the further excitation volume is determined automatically. The further excitation volume can be situated either in the MR image to be presented (i.e. can be included in the first excitation volume) or outside of the first excitation volume (which includes the volume of interest and the shown volume). One example of a position outside of the first excitation volume is the marking of moving spins; an example of an additional volume that is located in the first excitation volume (and therefore in the excited image) is the fat suppression of regions shown in the image, for example. The volume of interest can be established either automatically or by an operator.

The excitation of the additional volume that was determined automatically by the MR system takes place in Step 45. The excitation of the first volume that includes the volume of interest likewise takes place in Step 46, wherein the MR image of the volume of interest can be created subsequently in Step 47. The first volume can hereby be larger than the volume of interest, or of equal size. The method ends in Step 48. The image quality in the volume of interest is improved via the automatic determination of the further excitation volume since the influence of the magnetization from the further excitation volume can be suppressed, for example. The selection of the two volumes is likewise reproducible due to the automatic determination of at least one of the two volumes, and the measurement is accelerated via the automatic selection.

In FIG. 5 a flow chart is shown that indicates the steps to optimize the image quality in a partial volume. After the start of the method in Step 50, the acquisition of the overview image or overview images takes place in Step 51, similar to as in Step 41. Furthermore, the automatic determination of the anatomical structure or, respectively, of the multiple structures in the overview images takes place in Step 52. A first excitation volume is subsequently determined automatically that represents the volume that is shown later in the generated MR image. Furthermore, in Step 54 the volume of interest—a partial volume of the first excitation volume—is determined in the first excitation volume. For example, this can be the position of an individual organ as in the exemplary embodiment of FIG. 3. In a further step, the image presentation can be optimized in the volume of interest and not in the first excitation volume presented as a whole (Step 55). Among other things, this can be the optimization of the transmission module or, respectively, the optimization of the reception module for the volume of interest, or the optimization of the B0 homogeneity or of the gradient field. In one step (not shown), the automatically determined position of the volume of interest and of the further excitation volume are shown to the user before the measurement. He then has the possibility to accept this automatic selection without changes, or to make manual changes as desired. The acquisition of the MR images takes place subsequently in Step 56. The image quality in the volume of interest can be improved by optimizing the image generation for the volume of interest. The embodiments described in FIGS. 3 and 4 or, respectively, 4 and 5 can also be combined arbitrarily, meaning that the optimization for the volume of interest can be combined with the automatic determination of the volume of interest and the additional excitation volume (as is shown in FIG. 2).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate a magnetic resonance (MR) image that includes a volume of interest in an examination subject, said examination subject comprising an additional excitation volume, which differs at least partially from said volume of interest, comprising:

in a processor, automatically analyzing at least one MR overview image of the examination subject to automatically determine a position of at least one anatomical structure in the examination subject;

in said processor, automatically determining the volume of interest using the position of the at least one anatomical structure;

in the processor, automatically determining said additional excitation volume using the position of the at least one anatomical structure and not said volume of interest; and
generating an examination protocol in said processor configured to acquire the MR image that includes the volume of interest, by radio-frequency excitation of nuclear spins in the automatically determined additional excitation volume in order to achieve a desired magnetization of nuclear spins in the volume of interest, and making said protocol available at an output of the processor in an electronic form that causes a magnetic resonance apparatus to be operated according to said protocol.

2. A method as claimed in claim 1 comprising configuring said protocol to optimize, with respect to the volume of interest, radiation of said at least one RF pulse into the examination subject.

3. A method as claimed in claim 1 comprising configuring said protocol to optimize, with respect to the volume of interest, reception of MR signals from the examination subject.

4. A method as claimed in claim 1 comprising operating a magnetic resonance data acquisition unit with said protocol to acquire said MR image, while generating a static magnetic field in said data acquisition unit, having a magnetic field homogeneity, and, from said processor, optimizing said magnetic field homogeneity with respect to said volume of interest.

5. A method as claimed in claim 1 comprising, in said processor, configuring said protocol to optimize said magnetization in said additional excitation volume by optimizing an influence of said magnetization from said additional excitation volume on said volume of interest during acquisition of said MR image of said volume of interest.

6. A method as claimed in claim 5 comprising configuring said protocol to minimize the influence of said magnetization from said additional excitation volume in detection of MR signals from the volume of interest.

7. A method as claimed in claim 5 comprising exciting said nuclear spins in said additional volume to cause said magnetization in said additional excitation volume to flow into said volume of interest, with the magnetization flowing into said volume of interest differing from static magnetization prevailing in said volume of interest.

8. A method as claimed in claim 1 comprising operating a magnetic resonance data acquisition unit with said protocol to acquire MR data representing an MR image of said excitation volume that is larger than said volume of interest and that includes said volume of interest.

9. A magnetic resonance apparatus to generate a magnetic resonance (MR) image that includes a volume of interest in an examination subject, said examination subject comprising an additional excitation volume, which differs at least partially from said volume of interest, in which magnetization of nuclear spins is excited by at least one radio frequency (RF) pulse in order to achieve a desired magnetization in the volume of interest, comprising:
an MR data acquisition unit;
a computerized system configured to automatically analyze at least one MR overview image of the examination subject to automatically determine a position of at least one anatomical structure in the examination subject;
said computerized system being configured to automatically determine the volume of interest using the position of the at least one anatomical structure;
said computerized system being configured to automatically determine said additional excitation volume using the position of the at least one anatomical structure and not said volume of interest; and
said computerized system being configured to generate an examination protocol in said processor configured to acquire the MR image that includes the volume of interest, by radio-frequency excitation of nuclear spins in the automatically determined additional excitation volume in order to achieve a desired magnetization of nuclear spins in the volume of interest, and to operate said MR data acquisition unit according to said protocol.

10. A method to generate a magnetic resonance (MR) image of an excitation volume of an examination subject, said excitation volume comprising a volume of interest, wherein the volume of interest is a portion of said excitation volume and is smaller than said excitation volume, comprising:
in a processor, analyzing an MR overview image of the examination subject to automatically determine a position of at least one anatomical structure in the examination subject;
in said processor, automatically determining said volume of interest using the position of the at least one anatomical structure;
in said processor, generating a protocol, that includes activation of at least one magnetic field gradient, to operate an MR data acquisition unit to acquire said MR image, and configuring said protocol to optimize acquisition of MR signals from said excitation volume specifically for said volume of interest and not for a remainder of said excitation volume outside of said volume of interest by optimizing said magnetic field gradient to generate said magnetic field gradient in said volume of interest and not in said remainder of said excitation volume; and
making said protocol available at an output of the processor in an electronic form that causes a magnetic resonance apparatus to be operated according to said protocol.

11. A method as claimed in claim 10 comprising also configuring said protocol to optimize, with respect to said acquisition of the MR signal from the excitation volume, radiation of at least one radio frequency (RF) pulse into the volume of interest with a defined RF field distribution.

12. A method as claimed in claim 10 comprising also configuring said protocol to optimize, with respect to acquisition of said MR signals, reception of radio frequency (RF) signals as the received MR signals from the volume of interest.

13. A method as claimed in claim 10 comprising operating said MR data acquisition unit with said protocol to acquire said MR image, while generating a static magnetic field, having a magnetic field homogeneity, in said MR data acquisition unit, and, from said processor, and also optimizing said magnetic field homogeneity to cause an inhomogeneity of said magnetic field in said volume of interest to be less than a limit value, and to cause said inhomogeneity of said magnetic field not to be less than said limit value in said remainder of said excitation volume.

14. A method as claimed in claim 10 wherein said excitation volume comprises said volume of interest that is divided into multiple partial volumes.

15. A magnetic resonance apparatus to generate a magnetic resonance (MR) image of an excitation volume of an examination subject, said excitation volume comprising a volume of interest, wherein the volume of interest is a portion of said excitation volume and is smaller than said excitation volume, comprising:
an MR data acquisition unit comprising a gradient coil system;

a computerized system configured to analyze an MR overview image of the examination subject to automatically determine a position of at least one anatomical structure in the examination subject;

said computerized system being configured to automatically determine said volume of interest using the position of the at least one anatomical structure; and said computerized system being configured to generate a protocol, that includes activation of at least one magnetic field gradient by said gradient coil system, to operate an MR data acquisition unit to acquire said MR image, and configuring said protocol to optimize acquisition of MR signals from said excitation volume specifically for said volume of interest and not for a remainder of said excitation volume outside of said volume of interest by optimizing said magnetic field gradient to generate said magnetic field gradient in said volume of interest and not in said remainder of said excitation volume, and to operate said MR data acquisition unit according to said protocol.

* * * * *